US00PP37306P2

(12) United States Plant Patent
Guo

(10) Patent No.: US PP37,306 P2
(45) Date of Patent: Mar. 3, 2026

(54) ***KALANCHOE* PLANT NAMED 'KLEKB24054'**

(50) Latin Name: *Kalanchoe blossfeldiana*
Varietal Denomination: KLEKB24054

(71) Applicant: KLEMM + SOHN GMBH & CO. KG, Stuttgart (DE)

(72) Inventor: Huijuan Guo, Kornwestheim (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/317,124

(22) Filed: Sep. 2, 2025

(51) Int. Cl.
*A01H 5/02* (2018.01)
*A01H 5/12* (2018.01)
*A01H 6/32* (2018.01)

(52) U.S. Cl.
USPC ..... Plt./335
CPC ..... *A01H 6/324* (2018.05); *A01H 5/02* (2013.01); *A01H 5/12* (2013.01)

(58) Field of Classification Search
USPC ..... Plt./335
CPC ..... A01H 6/324; A01H 5/02
See application file for complete search history.

*Primary Examiner* — Keith O. Robinson
(74) *Attorney, Agent, or Firm* — Weatherly IP Solutions, LLC; James Weatherly

(57) ABSTRACT

A new *Kalanchoe* plant particularly distinguished by double flowers with purple color, small leaves, and a compact, upright, and free flowering plant habit, is disclosed.

1 Drawing Sheet

Genus and species: *Kalanchoe blossfeldiana.*
Variety denomination: 'KLEKB24054'.

BACKGROUND OF THE NEW PLANT

The present invention comprises a new and distinct variety of *Kalanchoe*, botanically known as *Kalanchoe blossfeldiana* and hereinafter referred to by the variety name 'KLEKB24054'. 'KLEKB24054' originated from a controlled cross between proprietary female *Kalanchoe* variety 'KA-2017-FV0003' (unpatented) and proprietary male *Kalanchoe* variety '1104-5' (unpatented) in Kenya in December 2019.

A plant line was selected in June 2020 and subsequently named 'KLEKB24054'. In July 2020, 'KLEKB24054' was first vegetatively propagated by vegetative terminal cuttings in Stuttgart, Germany. 'KLEKB24054' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Doubled flowers with purple color;
2. Small leaves; and
3. A compact, upright, and free flowering plant habit.

DESCRIPTION OF THE PHOTOGRAPH

This new *Kalanchoe* plant is illustrated by the accompanying photograph which shows an overall view of the plant. The photograph is of an approximately 12-week-old plant grown indoors in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLEKB24054'. The data which define these characteristics were collected from asexual reproductions carried out in Stuttgart, Germany. Data was collected in June 2025 on 14-week-old plants grown Stuttgart, Germany grown in a greenhouse. Color references are to The R.H.S. Colour Chart of The Royal Horticultural Society of London (R.H.S.), 5$^{th}$ edition (2007).

Classification:
*Family.*—Crassulaceae.
*Botanical.—Kalanchoe blossfeldiana.*
*Designation.*—'KLEKB24054'.

Parentage:
*Female parent.*—'KA-2017-FV0003' (unpatented).
*Male parent.*—'1104-5' (unpatented).

Propagation:
*Type.*—By vegetative terminal cuttings.
*Time to initiate roots, summer.*—About 10 days at temperatures about 20° C.
*Time to initiate roots, winter.*—About 13 days at temperatures about 20° C.
*Time to produce a rooted young plant, summer.*—About three weeks at temperatures about 20° C.
*Time to produce a rooted young plant, winter.*—About four weeks at temperatures about 21° C.
*Root description.*—Moderately freely branching.
*Root color.*—NN155C.

Plant description:
*Plant and growth habit.*—Medium compact and upright, moderate growth with a freely flowering habit with numerous cymes positioned above the foliar plane, triangular in shape with rounded crown, and can culture in pots with diameter 6.0 to 12.5 cm.

*Plant height at flowering*.—About 15.0 cm.

*Plant diameter at flowering*.—About 24.0 cm.

*Branching habit*.—Freely branching habit with about 13 lateral branches developing per plant.

*Lateral branch description*.—Length: 13.0 cm to 15.0 cm. Diameter: 6.5 cm. Internode length: 1 cm. Aspect: Mostly upright. Strength: Moderately strong. Texture: Smooth, glabrous. Color: Developing: 143A. Developed: 143C.

Leaf description:

*Arrangement*.—Opposite, single, generally symmetrical.

*Quantity of leaves per lateral branch*.—3 to 4 pairs.

*Length*.—4.0 cm to 10.0 cm.

*Width*.—1.5 cm to 4.0 cm.

*Shape*.—Ovate.

*Apex*.—Obtuse.

*Base*.—Obtuse.

*Margin*.—Broadly crenate.

*Texture*.—Upper surface: Smooth, glabrous, coriaceous, succulent, glossy. Lower surface: Smooth, glabrous, coriaceous, succulent, matte.

*Venation pattern*.—Pinnate.

*Color*.—Developing leaves: Upper surface: 143A. Lower surface: 137C. Fully developed leaves: Upper surface: 147A. Lower surface: 137B.

Petioles:

*Length*.—0.6 cm.

*Diameter*.—0.2 cm.

*Strength*.—Strong.

*Color*.—Upper surface: 147A. Lower surface: 137B.

Flower description:

*Flower arrangement and habit*.—Filled flowers arranged in axillary cymes, uniform and freely flowering habit, continuously for seven to eight weeks.

*Fragrance*.—Absent.

*Natural flowering season*.—Initiate and develop flowers under short day and long night conditions or during November and December in the Northern Hemisphere; buds and flowers can also be induced under artificial short day and long night conditions with about 14 hours darkness.

*Time to flower*.—Medium early flowering habit, plants begin flowering around 15 weeks after potting or sticking.

*Post-production longevity*.—Good post-production longevity, plants maintain good foliage and flower substance.

*Flower diameter*.—2.4 cm.

*Flower length (height)*.—1.8 cm.

*Flower bud*.—Length: 1.2 cm. Diameter: 0.6 cm. Shape: Initially oblong, becoming tubular ovoid with development. Texture: Smooth, glabrous, glossy. Color: 174A.

Petals:

*Arrangement*.—About 19 petals in multiple whorls.

*Length*.—1.0 cm.

*Width*.—0.8 cm.

*Aspect*.—Flat.

*Shape*.—Ovate to round.

*Apex*.—Acute.

*Base*.—Obtuse.

*Margin*.—Entire.

*Texture*.—Upper surface: Smooth, glabrous, glossy. Lower surface: Smooth, glabrous, matte.

*Color*.—When opening: Upper surface: 71B. Lower surface: 64C. Fully opened: Upper surface: N74A. Lower surface: 67C.

Sepals:

*Appearance*.—Four in a single whorl.

*Length*.—0.8 cm.

*Width*.—0.3 cm.

*Shape*.—Oblong, pointed.

*Apex*.—Acute.

*Base*.—Obtuse.

*Margin*.—Entire.

*Aspect*.—Upright.

*Texture*.—Upper surface: Smooth, glabrous, glossy. Lower surface: Smooth, glabrous, glossy.

*Color*.—Upper surface: 143A. Lower surface: 143B.

Peduncles:

*Length*.—0.7 cm to 1.0 cm.

*Diameter*.—0.1 cm.

*Aspect*.—Erect.

*Strength*.—Medium strong.

*Texture*.—Smooth and glabrous.

*Color*.—137A.

Reproductive organs:

*Androecium*.—Stamen number: 5 to 8 per flower. Filament color: 143C. Anther length: 0.1 cm. Anther shape: Elliptic. Anther color: 144D. Amount of pollen: Scarce. Pollen color: 12C.

*Gynoecium*.—Pistil number: 2 to 3. Pistil length: 0.9 cm. Style length: 0.3 cm. Style color: 144C. Stigma shape: Round and fluffy. Stigma color: 144C. Ovary color: 144B.

Seeds:

*Quantity per flower*.—If developed, up to 15 seeds.

*Length*.—About 0.01 cm.

*Diameter*.—About 0.05 cm.

*Texture*.—Rough.

*Color*.—166B.

Temperature tolerance: Plants have been observed to tolerate temperatures from 15° C. to 35° C.

Disease and pest/insect resistance: Plants have been observed to have tolerance to Powdery Mildew (*Erysiphe cichoraceaum*).

COMPARISON WITH PARENTAL LINES AND KNOWN VARIETY

'KLEKB24054' is distinguished from its parents as described in Table 1:

TABLE 1

Comparison with Parental Lines

| Characteristic | Variety 'KLEKB24054' | Female parent 'KA-2017-FV0003' | Male Parent '1104-5' |
|---|---|---|---|
| Flower doubleness | Double with more petals | Double | Single |
| Flower color | Purple | Dark pink | Dark purple |

'KLEKB24054' can be compared to the commercial variety 'Leonardo from Dummen Orange' (unpatented). Differences between the two varieties are described in Table 2:

TABLE 2

| Comparison with Similar Variety | | |
|---|---|---|
| Trait | 'KLEKB24054' | Commercial line 'Leonardo from Dümmen Orange' |
| Leaf size | Smaller than 'Leonardo from Dümmen Orange' | Bigger than 'KLEKB24054' |

TABLE 2-continued

| Comparison with Similar Variety | | |
|---|---|---|
| Trait | 'KLEKB24054' | Commercial line 'Leonardo from Dümmen Orange' |
| Vigor | More compact than 'Leonardo from Dümmen Orange' | Much more vigorous than 'KLEKB24054' |

I claim:

1. A new and distinct variety of *Kalanchoe* plant named 'KLEKB24054' as illustrated and described herein.

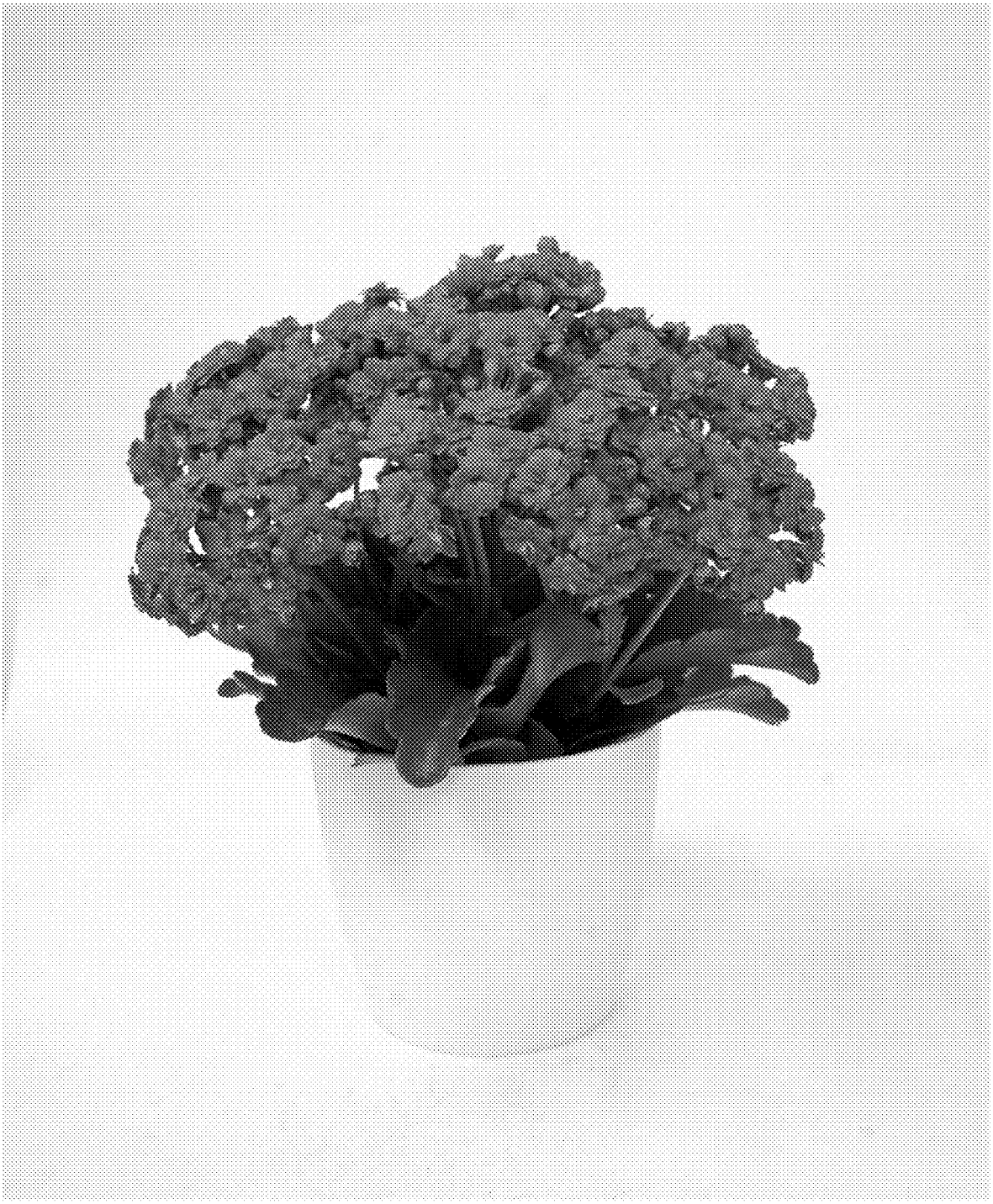

* * * * *